United States Patent
Jeong et al.

(10) Patent No.: US 7,378,162 B2
(45) Date of Patent: *May 27, 2008

(54) ORGANIC ELECTROLUMINESCENCE DEVICES USING RED PHOSPHORESCENCE COMPOUNDS

(75) Inventors: Hyun Cheol Jeong, Jinju-si (KR); Chun Gun Park, Seoul (KR); Jeong Dae Seo, Inchon (KR); Kyung Hoon Lee, Seoul (KR); Jae Man Lee, Seoul (KR); Jung Keun Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/128,421

(22) Filed: May 13, 2005

(65) Prior Publication Data
US 2006/0202194 A1   Sep. 14, 2006

(30) Foreign Application Priority Data
Mar. 8, 2005   (KR) ............ 10-2005-0019182

(51) Int. Cl.
*H05B 33/14* (2006.01)
*C09K 11/06* (2006.01)
*C07D 215/00* (2006.01)

(52) U.S. Cl. .............. 428/690; 428/917; 257/40; 313/504; 546/4; 546/10

(58) Field of Classification Search ................ 313/504; 546/4, 2, 10; 257/40; 428/690, 917
See application file for complete search history.

(56) References Cited

U.S. PATENT DOCUMENTS

2004/0127710 A1 * 7/2004 Park et al. ............ 546/2

FOREIGN PATENT DOCUMENTS

| JP | 2003-253145 | 9/2003 |
|---|---|---|
| WO | WO 03/033617 A1 | 4/2003 |
| WO | WO 03/040256 A2 | 5/2003 |

OTHER PUBLICATIONS

Lamansky, S., et al., "Synthesis and Characterization of Phosphorescent Cyclometalated Iridium Complexes," 2001 American Chemical Society, Inorg. Chem. 2001, 40, pp. 1704-1711, Mar. 26, 2001.
PCT Search Report.

* cited by examiner

*Primary Examiner*—Kamal A Saeed
*Assistant Examiner*—Joseph R Kosack
(74) *Attorney, Agent, or Firm*—Ked & Associates, LLP

(57) ABSTRACT

Red phosphorescene compounds and organic electro-luminescence device using the same are disclosed. In an organic electroluminescence device including an anode, a hole injecting layer, a hole transport layer, a light emitting layer, an electron transport layer, an electron injecting layer, and a cathode serially deposited on one another, the organic electroluminescence device may use a compound as a dopant of the light emitting layer.

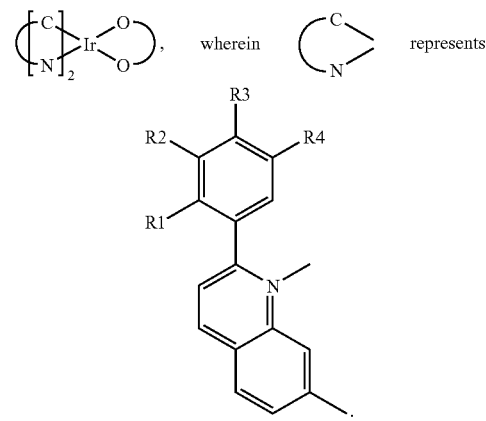

7 Claims, 2 Drawing Sheets

NPB

Copper(II) phthalocyanine (CuPc)

(btp)$_2$Ir(acac)

Alq3

BAlq3

CBP

ORGANIC ELECTROLUMINESCENCE DEVICES USING RED PHOSPHORESCENCE COMPOUNDS

This application claims the benefit of the Patent Korean Application No. 10-2005-0019182, filed on Mar. 8, 2005, which is hereby incorporated by reference as if fully set forth herein.

BACKGROUND OF THE INVENTION

1. Field of the Invention

The present invention relates to an organic electroluminescence device, and more particularly, to red phosphorescene compounds and organic electroluminescence device using the same. Most particularly, the present invention relates to red phosphorescence being used as a dopant of a light emitting layer of an organic electroluminescence device, which is formed by serially depositing an anode, a hole injecting layer, a hole transport layer, a light emitting layer, an electron transport layer, an electron injecting layer, and a cathode.

2. Discussion of the Related Art

Recently, as the size of display devices is becoming larger, the request for flat display devices that occupy lesser space is becoming more in demand. Such flat display devices include organic electroluminescence devices, which are also referred to as an organic light emitting diode (OLED). Technology of such organic electroluminescence devices is being developed at a vast rate and various prototypes have already been disclosed.

The organic electroluminescence device emits light when electric charge is injected into an organic layer, which is formed between an electron injecting electrode (cathode) and a hole injecting electrode (anode). More specifically, light is emitted when an electron and a hole form a pair and the newly created electron-hole pair decays. The organic electroluminescence device can be formed on a flexible transparent substrate such as plastic. The organic electroluminescence device can also be driven under a voltage lower than the voltage required in a plasma display panel or an inorganic electroluminescence (EL) display (i.e., a voltage lower than or equal to 10V). The organic electroluminescence device is advantageous in that it consumes less energy as compared to other display devices and that it provides excellent color representation. Moreover, since the organic EL device can reproduce pictures by using three colors (i.e., green, blue, and red), the organic EL device is widely acknowledged as a next generation color display device that can reproduce vivid images.

The process of fabricating such organic electroluminescence (EL) device will be described as follows:

(1) An anode material is coated over a transparent substrate. Generally, indium tin oxide (ITO) is used as the anode material.

(2) A hole injecting layer (HIL) is deposited on the anode material. The hole injecting layer is formed of a copper phthalocyanine (CuPc) layer having a thickness of 10 nanometers (nm) to 30 nanometers (nm).

(3) A hole transport layer (HTL) is then deposited. The hole transport layer is mostly formed of 4,4'-bis[N-(1-naphtyl)-N-phenylamino]-biphenyl (NPB), which is treated with vacuum evaporation and then coated to have a thickness of 30 nanometers (nm) to 60 nanometers (nm).

(4) Thereafter, an organic light emitting layer is formed. At this point, a dopant may be added if required. In case of green emission, the organic light emitting layer is generally formed of tris(8-hydroxy-quinolate)aluminum ($Alq_3$) which is vacuum evaporated to have a thickness of 30 nanometers (nm) to 60 nanometers (nm). And, MQD(N-Methylquinacridone) is used as the dopant (or impurity).

(5) Either an electron transport layer (ETL) and an electron injecting layer (EIL) are sequentially formed on the organic emitting layer, or an electron injecting/transport layer is formed on the organic light emitting layer. In case of green emission, the $Alq_3$ of step (4) has excellent electron transport ability. Therefore, the electron injecting and transport layers are not necessarily required.

(6) Finally, a layer cathode is coated, and a protective layer is coated over the entire structure.

A light emitting device emitting (or representing) the colors of blue, green, and red, respectively, is decided in accordance with the method of forming the light emitting layer in the above-described structure. As the light emitting material, an exciton is formed by a recombination of an electron and a hole, which are injected from each of the electrodes. A singlet exciton emits fluorescent light, and a triplet exciton emits phosphorescene light. The singlet exciton emitting fluorescent light has a 25% probability of formation, whereas the triplet exciton emitting phosphorescene light has a 75% probability of formation. Therefore, the triplet exciton provides greater light emitting efficiency as compared to the singlet exciton. Among such phosphorescene materials, red phosphorescence material may have greater light emitting efficiency than fluorescent materials. And so, the red phosphorescene material is being researched and studied as an important factor for enhancing the efficiency of the organic electroluminescence device.

When using such phosphorescene materials, high light emitting efficiency, high color purity, and extended durability are required. Most particularly, when using red phosphorescene materials, the visibility decreases as the color purity increases (i.e., the X value of the CIE chromacity coordinates becomes larger), thereby causing difficulty in providing high light emitting efficiency. Accordingly, red phosphorescence material that can provide characteristics of excellent chromacity coordinates (CIE color purity of X=0.65 or more), enhanced light emitting efficiency, and extended durability needs to be developed.

SUMMARY OF THE INVENTION

Accordingly, the present invention is directed to red phosphorescence compounds and an organic electro-luminescence device using the same that substantially obviate one or more problems due to limitations and disadvantages of the related art.

An object of the present invention is to provide an organic electroluminescence device having high color purity, high brightness, and long durability by combining the compound shown in Formula 1, which is used as a dopant in a light emitting layer of the organic EL device.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a red phosphorescence compound is indicated as Formula 1 below:

Formula 1

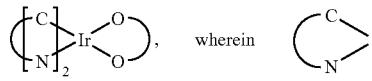 wherein  represents

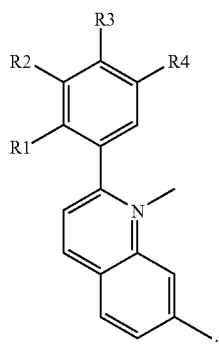

Herein each of R1, R2, R3, and R4 may be one of substituted or non-substituted C1 to C6 alkyl groups with disregard of one another. And, each of the C1 to c6 alkyl groups may be selected from a group consisting of methyl, ethyl, n-propyl, i-propyl, n-butyl, i-butyl, and t-butyl.

Additionally,

may include 2,4-pentanedione

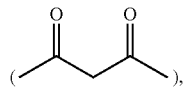

2,2,6,6,-tetra-methylheptane-3,5-dione

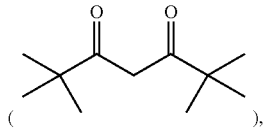

1,3-propanedione

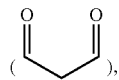, 1,3-butanedione

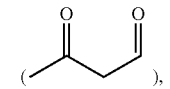, 3,5-heptanedione

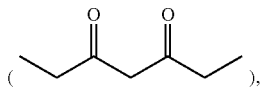, 1,1,1-trifluoro-2,4-pentanedione

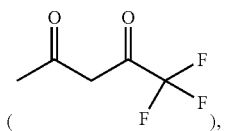, 1,1,1,5,5,5-hexafluoro-2,4-pentanedione

, and 2,2-dimethyl-3,5-hexanedione

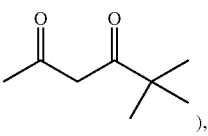,

Moveover,

may be any one of the following chemical formulas:

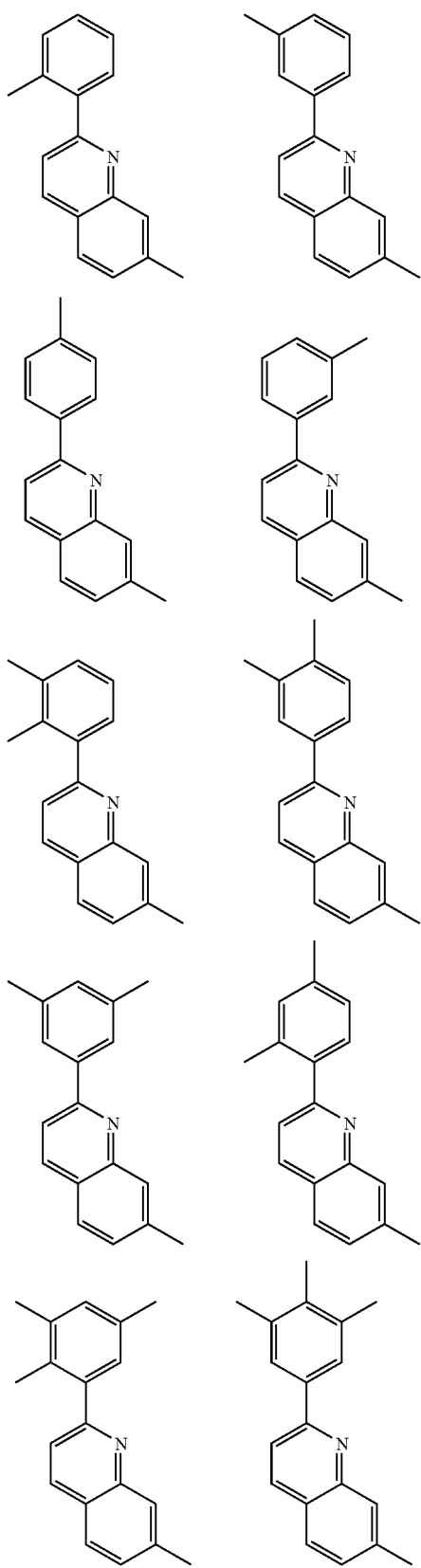
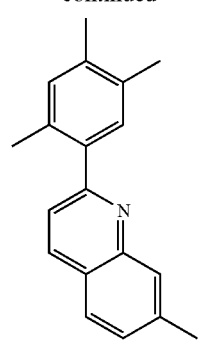
Furthermore, the Formula 1 may be any one of the following chemical formulas:
A-1
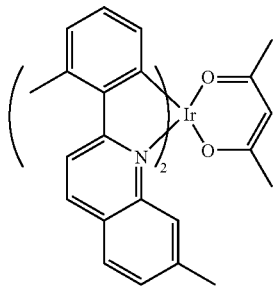
A-2
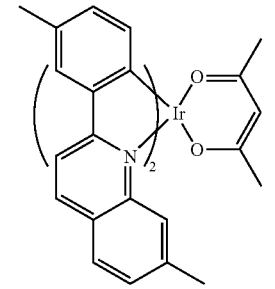
A-3
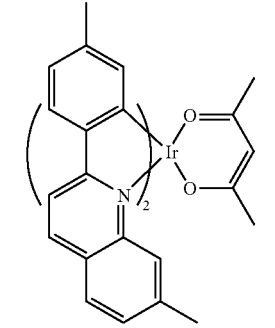

-continued
A-4
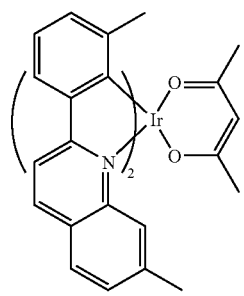
A-5
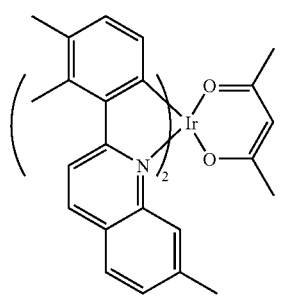
A-6
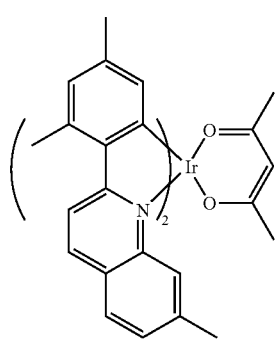
A-7
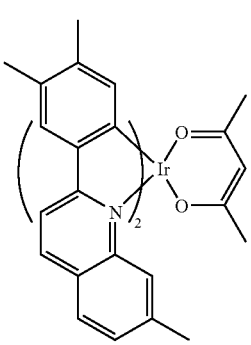
A-8
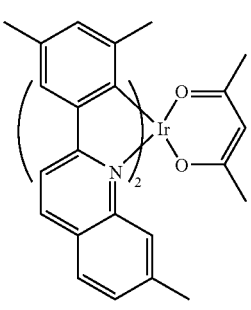
-continued
A-9
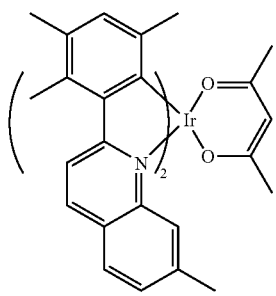
A-10
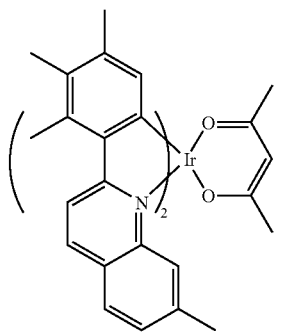
A-11
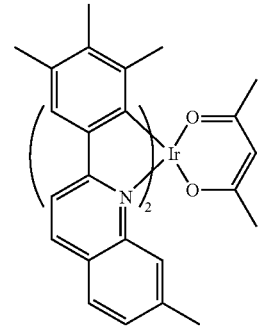
B-1
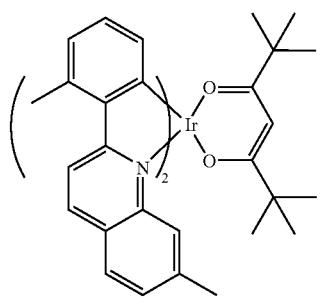
B-2
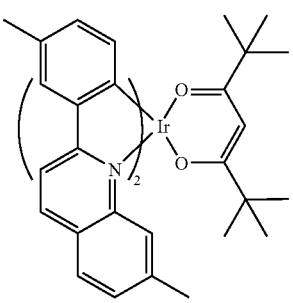

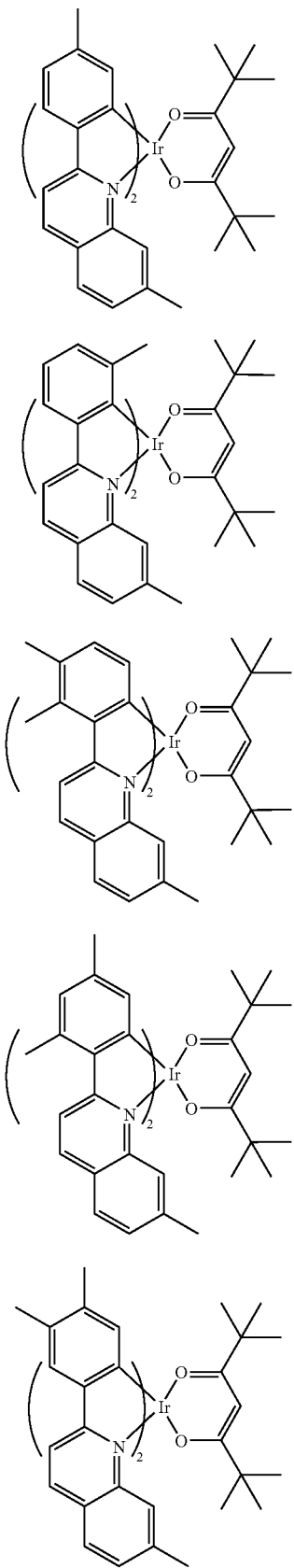
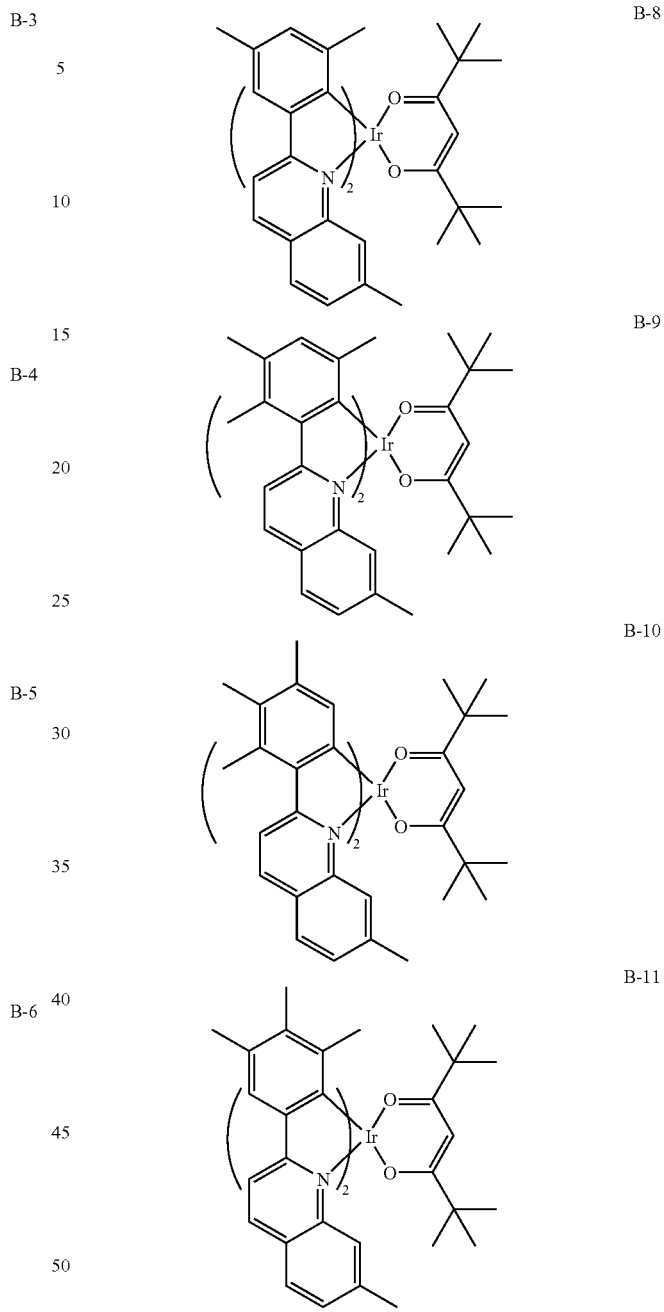

In another aspect of the present invention, in an organic electroluminescence device including an anode, a hole injecting layer, a hole transport layer, a light emitting layer, an electron transport layer, an electron injecting layer, and a cathode serially deposited on one another, the organic electroluminescence device may use any one of the above-described formulas as a dopant of the light emitting layer.

Herein, any one of Al and Zn metallic complexes and a carbazole derivative may be used as a host of the light emitting layer, and usage of the dopant may be within the range of 0.1 wt. % to 50 wt. %. The efficiency of the present invention may be provided when the amount of dopant used is within the above-described range. Furthermore, a ligand of each of the Al and Zn metallic complexes may include quinolyl, biphenyl, isoquinolyl, phenyl, methylquinolyl, dimethyl-quinolyl, dimethyl-isoquinolyl, and wherein the carbazole derivative may include CBP.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Figure 1:
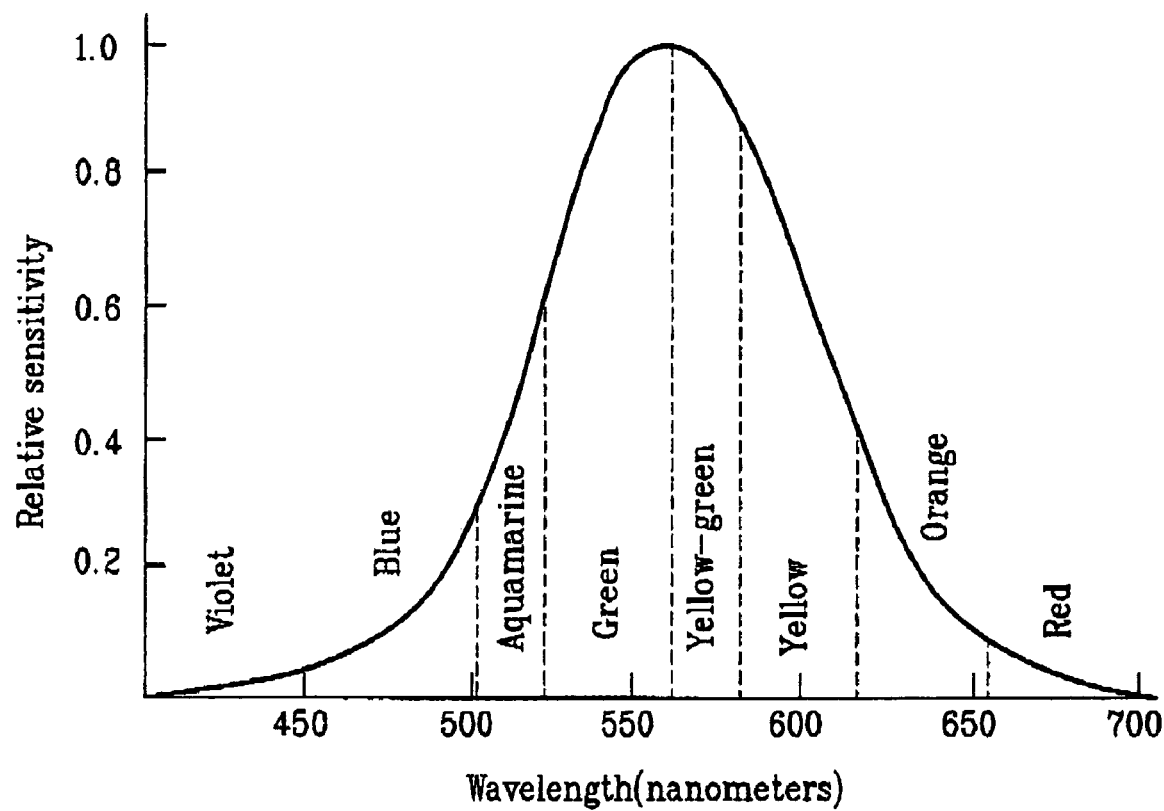
FIG. 1 illustrates a graph showing a decrease in visibility as color purity of an organic EL device increases (i.e., as the X value of chromaticity coordinates becomes greater)
Figure 2:
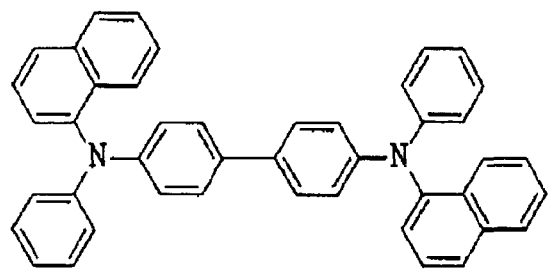
FIG. 2 illustrates structural formula of NPB, copper (II) phthalocyanine (CuPc), (bpt)$_2$Ir(acac), Alq$_3$, BAlq, and CBP, which are compounds used in embodiments of the present invention.
Figure 2:
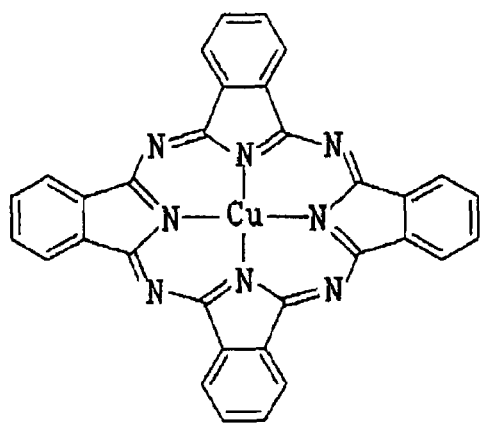
Figure 2:
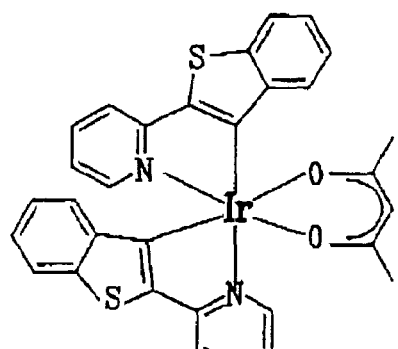
Figure 2:
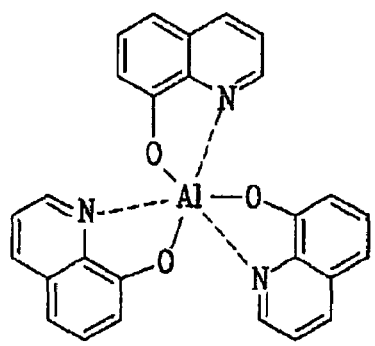
Figure 2:
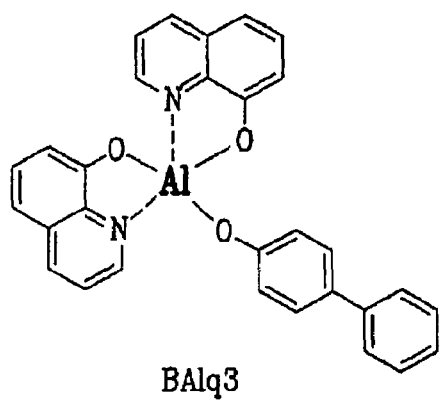
Figure 2:
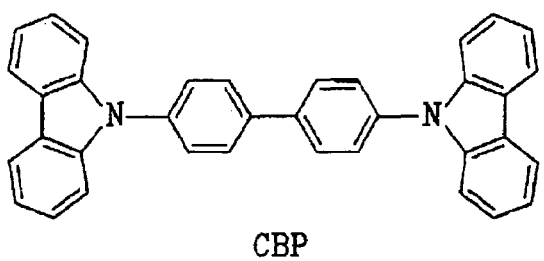

Reference will now be made in detail to the preferred embodiments of the present invention, examples of which are illustrated in the accompanying drawings. Wherever possible, the same reference numbers will be used throughout the drawings to refer to the same or like parts.

A method of combining the red phosphorescence compound according to the present invention will now be described. An iridium (lll)(2-(3-methylphenyl)-7-methyl-quinolinato-N,C$^2$)(2,4-pentanedionate-0,0) compound, which is shown as A-2 among the red phosphorescene compounds used in the organic EL device according to the present invention.

COMBINATION EXAMPLE

1. Combination of 2-(3-methylphenyl)-7-methyl-quinoline

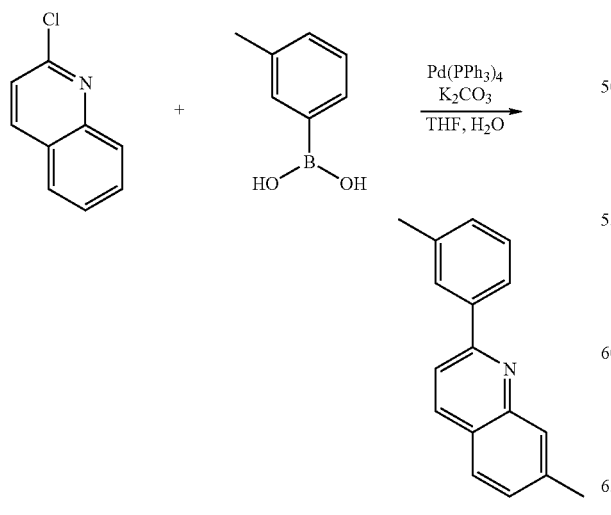

3-methyl-phenyl-boric acid (1.3 mmol), 2-chloro-7-methyl-quinoline (1 mmol), tetrakis (triphenyl phosphine) palladium(0) (0.05 mmol), and potassium carbonate (3 mmol) are dissolved in a two-neck round bottom flask containing THF (30 ml) and H$_2$O (10 ml). The mixture is then stirred for 24 hours in a bath of 100 degrees Celsius (° C.). Subsequently, when reaction no longer occurs, the THF and toluene are discarded. The mixture is extracted by using dichloromethane and water, which is then treated with vacuum distillation. Then, after filtering the mixture with a silica gel column, a solvent is treated with vacuum distillation. Thereafter, by using dichloromethane and petroleum ether, the mixture is re-crystallized and filtered, thereby yielding solid 2-(3-methylphenyl)-7-methyl-quinoline.

2. Formation of Chloro-cross-linked Dimer Complex

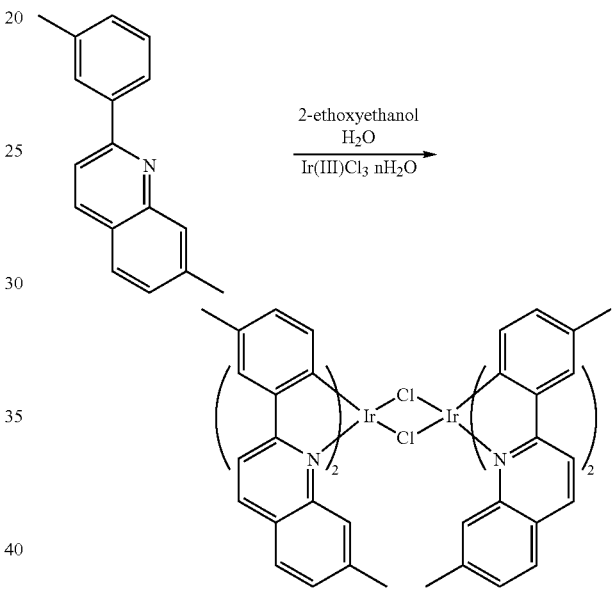

Iridium chloride (1 mmol) and 2-(3-methylphenyl)-7-methyl-quinoline (2.5 mmol) are mixed in a 3:1 liquid mixture (30 ml) of 2-ethoxyethanol and distilled water. Then, the mixture is refluxed for 24 hours. Thereafter, water is added so as to filter the solid form that is produced. Subsequently, the solid form is washed by using methanol and petroleum ether, thereby yielding the chloro-cross-linked dimer complex.

3. Formation of Iridium (lll)(2-(3-methylphenyl)-7-methyl-quinolinato-N,C$^2$)(2,4-pentanedionate-0,0)

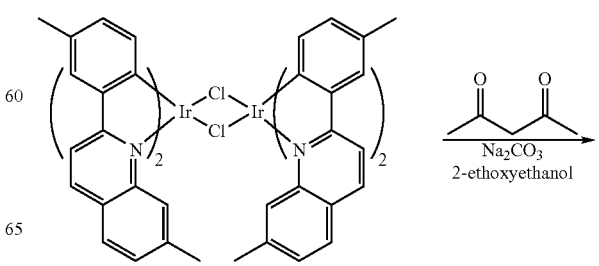

-continued

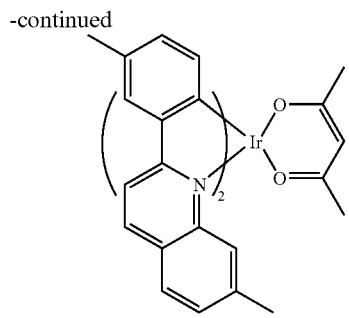

A chloro-cross-linked dimer complex (1 mmol), 2,4-pentane dione (3 mmol), and Na$_2$CO$_3$ (6 mmol) are mixed into 2-ethoxyethanol (30 ml) and refluxed for 24 hours. The refluxed mixture is then cooled at room temperature. Thereafter, distilled water is added to the cooled mixture, which is filtered so as to yield a solid form. Subsequently, the solid form is dissolved in dichloromethane, which is then filtered by using silica gel. Afterwards, the dichloromethane is treated with vacuum suction, and the solid form is washed by using methanol and petroleum ether, so as to obtain the chemical compound.

Hereinafter, examples of preferred embodiments will be given to describe the present invention. It will be apparent that the present invention is not limited only to the proposed embodiments.

EMBODIMENTS

1. First Embodiment

An ITO glass substrate is patterned to have a light emitting area of 3 mm×3 mm. Then, the patterned ITO glass substrate is washed. Subsequently, the substrate is mounted on a vacuum chamber. The standard pressure is set to 1×10$^{-6}$ torr. Thereafter, layers of organic matter are formed on the ITO substrate in the order of CuPC (200 Å), NPB (400 Å), CBP+(btp)$_2$Ir(acac)(7%) (200 Å), a hole blocking layer (100 Å), Alq$_3$ (300 Å), LiF (5 Å), and Al (1000 Å).

When forming a hole blocking layer using BAlq, the brightness is equal to 689 cd/m$^2$ (8.1 V) at 0.9 mA. At this point, CIE x=0.651, y=0.329. Furthermore, the durability (half of the initial brightness) lasts for 1600 hours at 2000 cd/m$^2$.

2. Second Embodiment

An ITO glass substrate is patterned to have a light emitting area of 3 mm×3 mm. Then, the patterned ITO glass substrate is washed. Subsequently, the substrate is mounted on a vacuum chamber. The standard pressure is set to 1×10$^{-6}$ torr. Thereafter, layers of organic matter are formed on the ITO substrate in the order of CuPC (200 Å), NPB (400 Å), BAlq+A-2(7%) (200 Å), Alq$_3$ (300 Å), LiF (5 Å), and Al (1000 Å).

At 0.9 mA, the brightness is equal to 1448 cd/m$^2$ (6.2 V). At this point, CIE x=0.644, y=0.353. Furthermore, the durability (half of the initial brightness) lasts for 8000 hours at 2000 cd/m$^2$.

3. Third Embodiment

An ITO glass substrate is patterned to have a light emitting area of 3 mm×3 mm. Then, the patterned ITO glass substrate is washed. Subsequently, the substrate is mounted on a vacuum chamber. The standard pressure is set to 1×10$^{-6}$ torr. Thereafter, layers of organic matter are formed on the ITO substrate in the order of CuPC (200 Å), NPB (400 Å), BAlq+A-5(7%) (200 Å), Alq$_3$ (300 Å), LiF (5 Å), and Al (1000 Å).

At 0.9 mA, the brightness is equal to 1378 cd/m$^2$ (6.0 V). At this point, CIE x=0.659, y=0.351. Furthermore, the durability (half of the initial brightness) lasts for 7000 hours at 2000 cd/m$^2$.

COMPARISON EXAMPLE

An ITO glass substrate is patterned to have a light emitting area of 3 mm×3 mm. Then, the patterned ITO glass substrate is washed. Subsequently, the substrate is mounted on a vacuum chamber. The standard pressure is set to 1×10$^{-6}$ torr. Thereafter, layers of organic matter are formed on the ITO substrate in the order of CuPC (200 Å), NPB (400 Å), BAlq+(btp)$_2$Ir(acac) (7%) (200 Å), Alq$_3$ (300 Å), LiF (5 Å), and Al (1000 Å).

At 0.9 mA, the brightness is equal to 780 cd/m$^2$ (7.5 V). At this point, CIE x=0.659, y=0.329. Furthermore, the durability (half of the initial brightness) lasts for 2500 hours at 2000 cd/m$^2$.

In accordance with the above-described embodiments and comparison example, the characteristics of efficiency, chromacity coordinates, brightness, and durability are shown in Table 1 below.

TABLE 1

| Device | Voltage (V) | Current (mA) | Brightness (cd/m$^2$) | Current Efficiency (cd/A) | Power Efficiency (1 m/W) | CIE (X) | CIE (Y) | Durability(h) ½ of initial brightness |
|---|---|---|---|---|---|---|---|---|
| First Embodiment | 8.1 | 0.9 | 690 | 6.9 | 2.7 | 0.651 | 0.329 | 1600 |
| Second Embodiment | 6.2 | 0.9 | 1450 | 14.5 | 7.3 | 0.644 | 0.353 | 8000 |
| Third Embodiment | 6.0 | 0.9 | 1378 | 13.8 | 7.2 | 0.659 | 0.351 | 7000 |
| Comparison Example | 7.5 | 0.9 | 780 | 7.8 | 3.3 | 0.659 | 0.329 | 2500 |

As shown in Table 1, the device is operated with high efficiency at a low voltage even when the color purity is high. Furthermore, the current efficiency of the second embodiment has increased by 100% or more as compared to the comparison example. Additionally, the durability of the second embodiment has increased to three times that of the comparison example.

Table 2 below shows the characteristics of efficiency, chromacity coordinates, and brightness in accordance with the increase in voltage and electric current in the organic electroluminescence device according to the second embodiment of the present invention.

TABLE 2

| Voltage (V) | Current (A(mA/cm²) | Brightness (cd/m²) | Current Efficiency (cd/A) | Power Efficiency (1 m/W) | CIE (X) | CIE (Y) |
|---|---|---|---|---|---|---|
| 5.0 | 1.111 | 168.6 | 15.2 | 9.5 | 0.645 | 0.353 |
| 5.5 | 3.333 | 500.8 | 15.0 | 8.5 | 0.645 | 0.353 |
| 6.0 | 7.777 | 1139 | 14.6 | 7.6 | 0.644 | 0.354 |
| 6.5 | 16.666 | 2309 | 13.9 | 6.6 | 0.643 | 0.354 |
| 7.0 | 33.333 | 4275 | 12.9 | 5.7 | 0.643 | 0.355 |
| 7.5 | 66.666 | 7664 | 11.5 | 4.8 | 0.641 | 0.356 |

As shown in Table 2, the second embodiment provides excellent efficiency, and the chromacity coordinates according to the driving voltage also maintains high color purity.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An organic electroluminescent device comprising a light emitting layer, the light emitting layer comprising a red phosphorescence compound of Formula 1 below as a dopant:

Formula 1 wherein each of R1, R2, R3, and R4 is independently selected from the group consisting of hydrogen and substituted or non-substituted C1 to C6 alkyl groups, and wherein represents an alkanedione selected from the group consisting of 2,4-pentanedione, 2,2,6,6,-tetra-methylheptane-3,5-dione, 3,5-heptanedione, 1,1,1-trifluoro-2,4-pentanedione, 1,1,1,5,5,5-hexafluoro-2,4-pentanedione, and 2,2-dimethyl-3,5-hexanedione.

2. The organic electroluminescent device of claim 1, wherein any one of Al and Zn metallic complexes and carbazole derivatives is used as a host of the light emitting layer.

3. The organic electroluminescent device of claim 1, wherein any one of Al and Zn metallic complexes and a carbazole derivative is used as a host of the light emitting layer, and wherein usage of the dopant within the range of 0.1 wt. % to 50 wt. %.

4. The organic electroluminescent device of claim 2, wherein a ligand in each of the Al and Zn metallic complexes comprises quinolyl, biphenyl, isoquinolyl, phenyl, methylquinolyl, dimethylquinolyl, dimethyl-isoquinolyl, and wherein the carbazole derivative comprises CBP.

5. The organic electroluminescent device of claim 1, wherein each of the C1 to C6 alkyl groups is selected from a group consisting of methyl, ethyl, n-propyl, i-propyl, n-butyl, i-butyl, and t-butyl.

6. The organic electroluminescent device of claim 1, wherein is any one of the following chemical formulae:

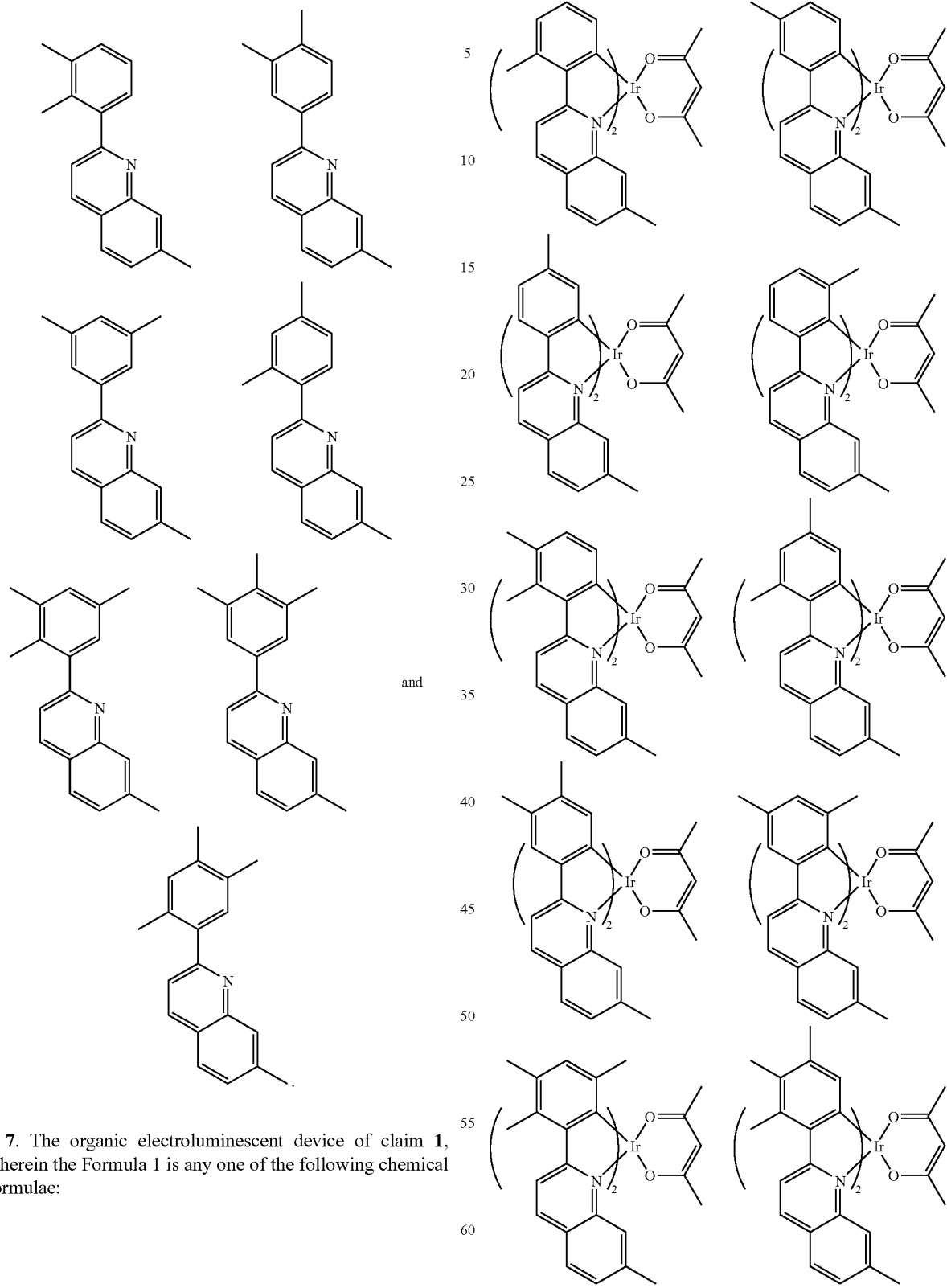
7. The organic electroluminescent device of claim 1, wherein the Formula 1 is any one of the following chemical formulae:

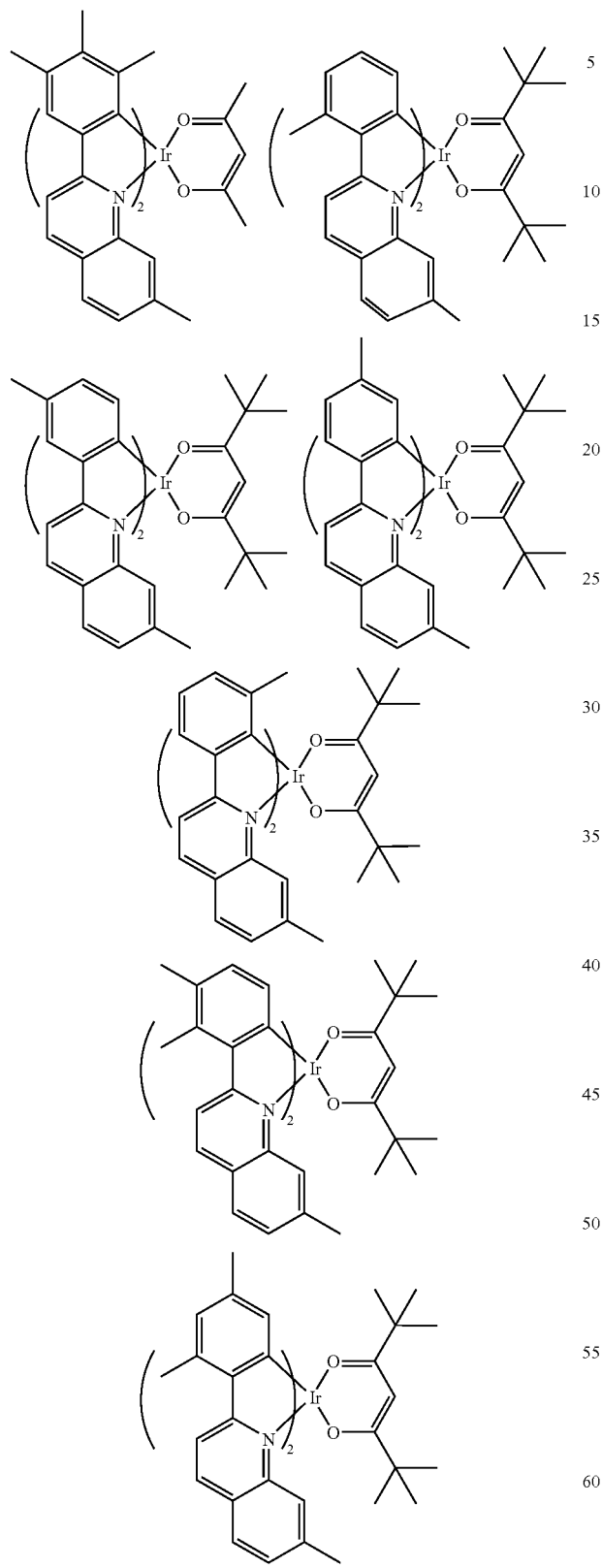
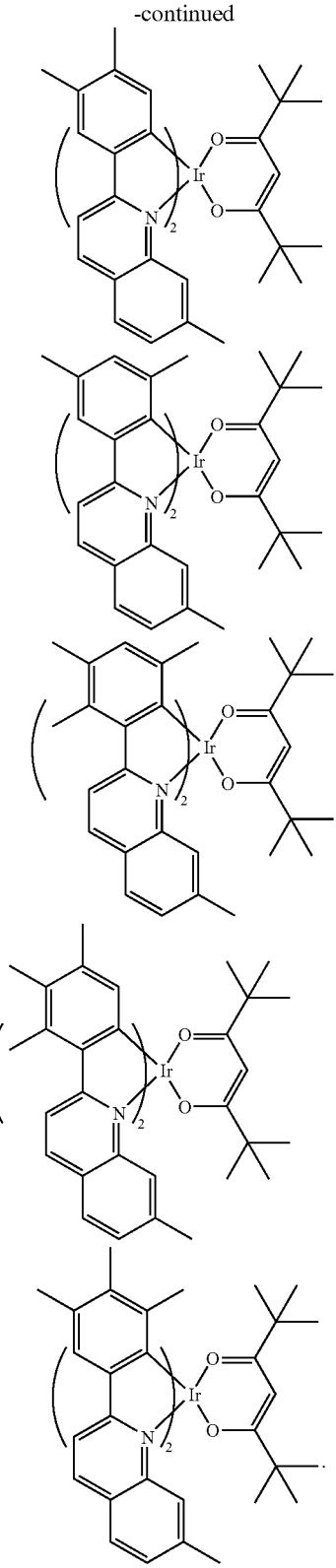
* * * * *